(12) United States Patent
Becker et al.

(10) Patent No.: US 8,647,116 B2
(45) Date of Patent: Feb. 11, 2014

(54) ROTARY ENDODONTIC FILE WITH FRICTIONAL GRIP

(75) Inventors: Arik Becker, Kibbutz Afikim (IL); Haim Levy, Pardes Hanna (IL); Simon Rothenstein, Rosh HaAyin (IL)

(73) Assignee: Medic NRG Ltd, Kibbutz Afikim (IL)

( * ) Notice: Subject to any disclaimer, the term of this patent is extended or adjusted under 35 U.S.C. 154(b) by 486 days.

(21) Appl. No.: 12/713,490

(22) Filed: Feb. 26, 2010

(65) Prior Publication Data

US 2011/0212413 A1 Sep. 1, 2011

(30) Foreign Application Priority Data

Feb. 25, 2010 (IL) .......................................... 204195

(51) Int. Cl.
*A61C 5/02* (2006.01)
(52) U.S. Cl.
USPC ........................................................ 433/102
(58) Field of Classification Search
USPC ........ 433/102, 224; 606/79–81, 96, 167, 170, 606/180; 132/76.4, 76.5; 407/29.1–29.5; 15/23, 93.1, 104.066, 104.09, 104.095; 16/110.1, 422, 426, 427, 430, 431; 30/342; 220/756, 752; 294/14, 15, 26, 294/100; 600/188; 604/585
See application file for complete search history.

(56) References Cited

U.S. PATENT DOCUMENTS

| | | | |
|---|---|---|---|
| 1,168,052 A * | 1/1916 | bolls et al. .................... 433/118 |
| 1,771,182 A | 7/1930 | Lentulo |
| 2,611,960 A | 9/1952 | Herndon |
| 3,306,375 A * | 2/1967 | Elmer .............................. 173/59 |
| 3,330,040 A * | 7/1967 | Kahn ............................. 433/224 |
| 3,850,054 A * | 11/1974 | Weissman .................... 76/108.1 |
| 3,884,230 A | 5/1975 | Wulff |
| 4,145,061 A | 3/1979 | Schneider |
| 4,185,388 A * | 1/1980 | Jarby ............................ 433/125 |
| 4,190,958 A | 3/1980 | Martin et al. |
| 4,202,101 A * | 5/1980 | Weissman ..................... 433/225 |
| 4,292,027 A * | 9/1981 | Richmond .................... 433/127 |
| 4,447,208 A * | 5/1984 | Kawai ........................... 433/166 |
| 4,636,171 A * | 1/1987 | Martin ......................... 433/134 |
| 4,830,615 A | 5/1989 | Feinman et al. |
| 4,850,867 A * | 7/1989 | Senia et al. .................... 433/102 |
| 5,211,560 A * | 5/1993 | Lowder et al. ............... 433/166 |
| 5,334,020 A * | 8/1994 | Eckert .......................... 433/166 |
| 5,482,461 A * | 1/1996 | Yale ............................. 433/125 |
| 5,501,597 A | 3/1996 | Wilson |

(Continued)

FOREIGN PATENT DOCUMENTS

WO 2008/102352 A1 8/2008
WO WO 2008102352 A1 * 8/2008 ............... A61C 5/02

OTHER PUBLICATIONS

Search Report & Written Opinion pertaining to PCT/IL2011/000179 dated Jul. 20, 2011.

*Primary Examiner* — Cris L Rodriguez
*Assistant Examiner* — Matthew Saunders
(74) *Attorney, Agent, or Firm* — Dinsmore & Shohl LLP (57) ABSTRACT

An endodontic file (10) has at least a central longitudinal cord (12), a helically wound wire (14) at least partially surrounding the cord and an elastomeric grip (16) partially covering the helically wound wire near a first end thereof and having an outer diameter that is slightly wider than an internal diameter of a barrel of a dental instrument whereby on insertion into the barrel it is supported therein only by friction.

34 Claims, 8 Drawing Sheets

(56) References Cited

U.S. PATENT DOCUMENTS

| | | | |
|---|---|---|---|
| 5,516,287 A * | 5/1996 | Zdarsky | 433/102 |
| 5,533,897 A | 7/1996 | Zdarsky | |
| 5,775,903 A * | 7/1998 | Atkins | 433/102 |
| 5,915,964 A * | 6/1999 | Walia | 433/102 |
| 6,179,617 B1 * | 1/2001 | Ruddle | 433/224 |
| 6,213,771 B1 * | 4/2001 | Fischer | 433/75 |
| 6,443,730 B2 * | 9/2002 | Davidson | 433/102 |
| 6,464,498 B1 | 10/2002 | Pond | |
| 6,575,748 B1 * | 6/2003 | Filhol | 433/102 |
| 6,579,092 B1 * | 6/2003 | Senia et al. | 433/102 |
| 6,589,052 B1 * | 7/2003 | Wilcko | 433/102 |
| 6,746,245 B2 | 6/2004 | Riitano et al. | |
| 6,966,774 B2 | 11/2005 | Brock et al. | |
| 6,981,869 B2 | 1/2006 | Ruddle | |
| 7,137,815 B2 | 11/2006 | Matsutani et al. | |
| 7,226,289 B2 * | 6/2007 | Bills | 433/102 |
| 2003/0203155 A1 * | 10/2003 | Kobe et al. | 428/119 |
| 2005/0221256 A1 * | 10/2005 | Kangasniemi | 433/102 |
| 2006/0127843 A1 * | 6/2006 | Rosenblood et al. | 433/102 |
| 2006/0216668 A1 * | 9/2006 | Scianamblo | 433/102 |
| 2007/0015107 A1 * | 1/2007 | Mannschedel et al. | 433/102 |
| 2007/0099149 A1 * | 5/2007 | Levy et al. | 433/102 |
| 2007/0101827 A1 * | 5/2007 | Quan et al. | 76/108.1 |

* cited by examiner

ROTARY ENDODONTIC FILE WITH FRICTIONAL GRIP

CROSS-REFERENCE TO RELATED APPLICATIONS

This application claims the benefit of Israeli Patent No. 204195 filed Feb. 25, 2010, which is incorporated by reference herein in its entirety.

FIELD OF THE INVENTION

The present invention relates to endodontic devices and more particularly to a rotary endodontic file with a frictional elastomer grip to be utilized with a standard dental handpiece.

BACKGROUND OF THE INVENTION

Modern endodontic treatment involves removal of the damaged pulp, followed by cleaning and shaping of the root canal space, irrigating, and filling with biocompatible material such as gutta-percha and a root canal sealer.

Shaping of the canal is performed either manually, using a series of stainless steel hand-held files, or mechanically, using rotary nickel-titanium files adapted to fit a standard or dedicated dental handpiece.

The manual process relies on the experience of the dentist, is physically difficult to perform and is time-consuming. The use of files requires repeated changing between numerous different rat-tail files, progressively increasing from the smallest to the largest. Its reach to the apical constriction for educate widening and removal of the smear layer is limited. The reason for such limitations relates to the moderate elasticity of the steel files and the risk of fracture when excessive force is applied.

Although the field of elastic rotary nickel-titanium endodontic files has developed greatly over the last few years, fracture (separation) of nickel-titanium rotary files is still often reported, and hence the use of such is restricted. In order to overcome the fracture problem, a large range of dedicated handpiece systems, powered by slow speed transaction equipped with torque and speed control limitation circuits, have been developed, requiring a high level of professional skill for their operation. As a result, the cost of files and the related equipment per endodontic treatment became significantly higher and are typically operated only by experts in the endodontic field, while ordinary dentists use standard handpiece in a risky procedure.

Additionally the round cross-section of the file prevents adequate cleaning when the canal cross-section is oval or narrow in shape. In such cases, enlargement of the canal cross-section to accept the round cross-section of the file, may weaken or perforate the wall or the apical portion of the canal. The same risk of perforation applies in case of a curved root canal, where the file tends to follow the path of least resistance, acting rigorously on the convex walls within the reach of the file, and insufficiently over the concave portions.

US20070099149 entitled "Endodontic device and method of utilizing and manufacturing same" corresponding to IL 171705 in the name of the present applicant discloses an endodontic device for cleaning, filing or reaming root canals. The device includes one or more metallic, flexible strands having an edge, a working section, a connecting section and a coupling head connected thereto. The strands are coated along the working section with a thin layer of a binder having abrasive particles embedded therein. The flexible, longitudinal strands are so constructed that their outer surfaces serve as active filing surfaces.

In operation the strand section of the endodontic file is inserted into the root canal to the apex, and the strand or strands are mechanically rotated by a handpiece to a high speed. The thin, flexible portion of the device is centrifugally thrown against the canal wall following the natural curvature and complex cross-section of the root canal in exact manner. The whole contents of US20070099149 are incorporated herein by reference.

WO2008/102352 entitled "Endodontic file" corresponding to IL 181439 in the name of the present applicant and likewise incorporated herein by reference, it is further suggested to use an endodontic file comprising at least one cord and a wire wound around at least a major portion of the cord, the wire having an abrasive outer surface.

However, in both the above-mentioned references, the file is firmly gripped and forcibly rotated by a standard or dedicated high speed handpiece, normally having no means or even technical ability, while in such high rotation speed, to control the delivered torque due to the high inertia of the motor itself. As a result although intended for high speed operation, the file may break if for some reason sticking or locking of the cord in the root canal occurs during operation.

Consequently, there exists a need for limiting the transmitted torque in order to prevent breakage of the wire endodontic file in case of sticking. Such an additional safety measure in operation will encourage use of a high-speed rotary endodontic file by those dentists who currently refrain from using such devices for fear of damaging the dentine layer or perforating the root canal.

SUMMARY OF THE INVENTION

In accordance with the invention there is therefore provided an endodontic file comprising at least a central longitudinal cord, a helically wound wire at least partially surrounding the cord and an elastomeric grip partially covering the helically wound wire near a first end thereof and having an outer diameter that is slightly wider than an internal diameter of a barrel of a dental instrument whereby on insertion into the barrel it is supported therein only by friction.

Advantageously, the elastomer grip is cylindrical with a conical extension tapering to a very thin cover towards an active portion of the helically wound wire. Optionally longitudinal fins of the same elastomer material are formed in a circular array around the cylindrical portion of the grip.

The invention further provides a method for safely limiting the torque imparted to an endodontic file according to the invention utilized with a dental instrument, the method comprising:

inserting the grip of said file into the mounting barrel of a dental instrument; and imparting rotational movement to the file based only on friction, wherein the imparted torque is limited by the percentage of squeeze of said elastomer grip during insertion to the mounting barrel and by the coefficient of friction between the grip elastomer material and the metal barrel of the handpiece, such that if the shear force between the file and the root canal increases beyond a predetermined value, the grip will slip in the handpiece barrel and no breakage damage will occur to the file, nor any undesirable damage to the dentine layer.

The invention still further provides a method of a root canal of a tooth during an endodontic treatment using the endodontic file according to the invention, the method comprising:

opening the root canal using a hand-held file of the smallest applicable thickness; frictionally attaching the endodontic file to a standard or dedicated handpiece;

inserting the working section of the file into the root canal;

setting the handpiece to rotate at speed of between 6000 to 30000 rpm; providing irrigation;

using resultant centrifugal forces acting about the slender working section of the file, which is thrown against the internal dentine layer of the canal wall following the natural curvature and complex cross-section of the root canal in exact manner, thereby providing complete canal preparation in a single time-saving procedure.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the following description of some embodiments, identical components that appear in more than one figure or that share similar functionality will be referenced by identical reference symbols.

Figure 1:
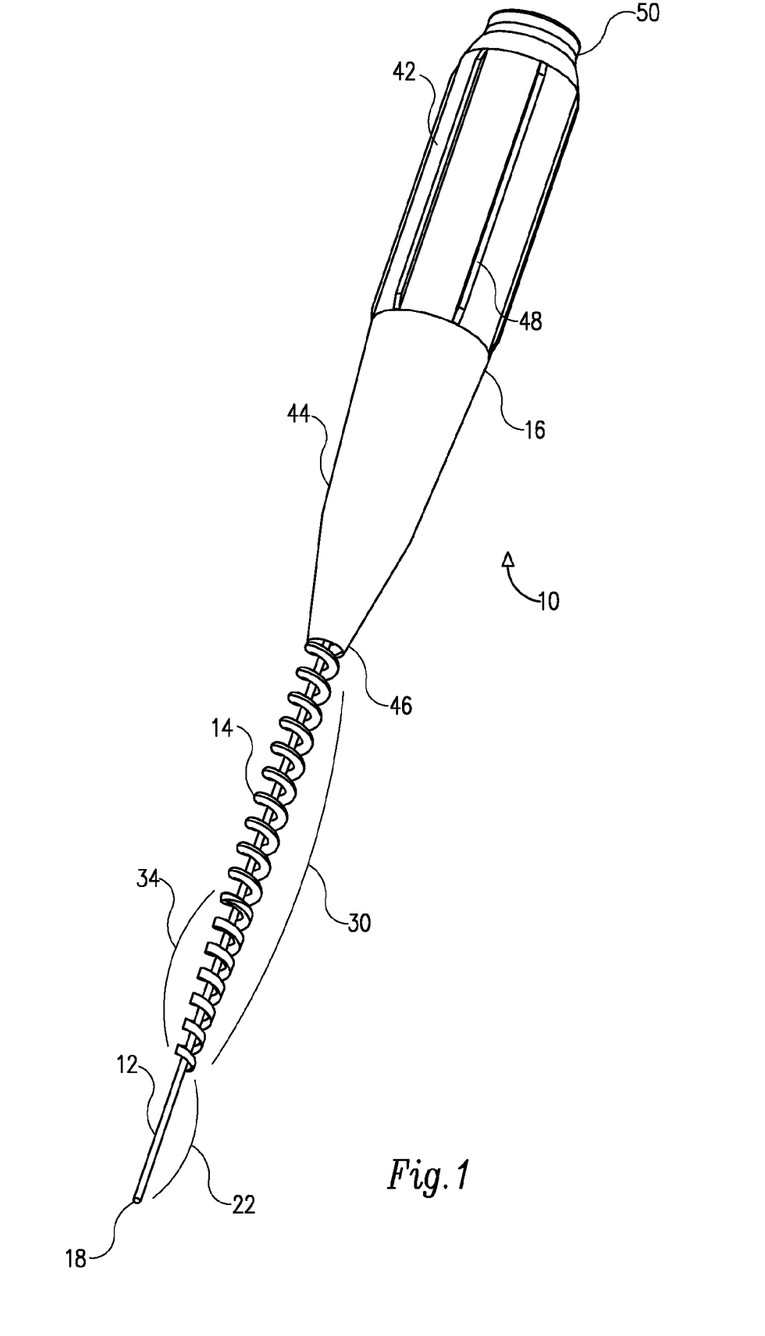
FIG. 1 is a perspective view of an assembled endodontic file according to an embodiment of the present invention.
Figure 2:
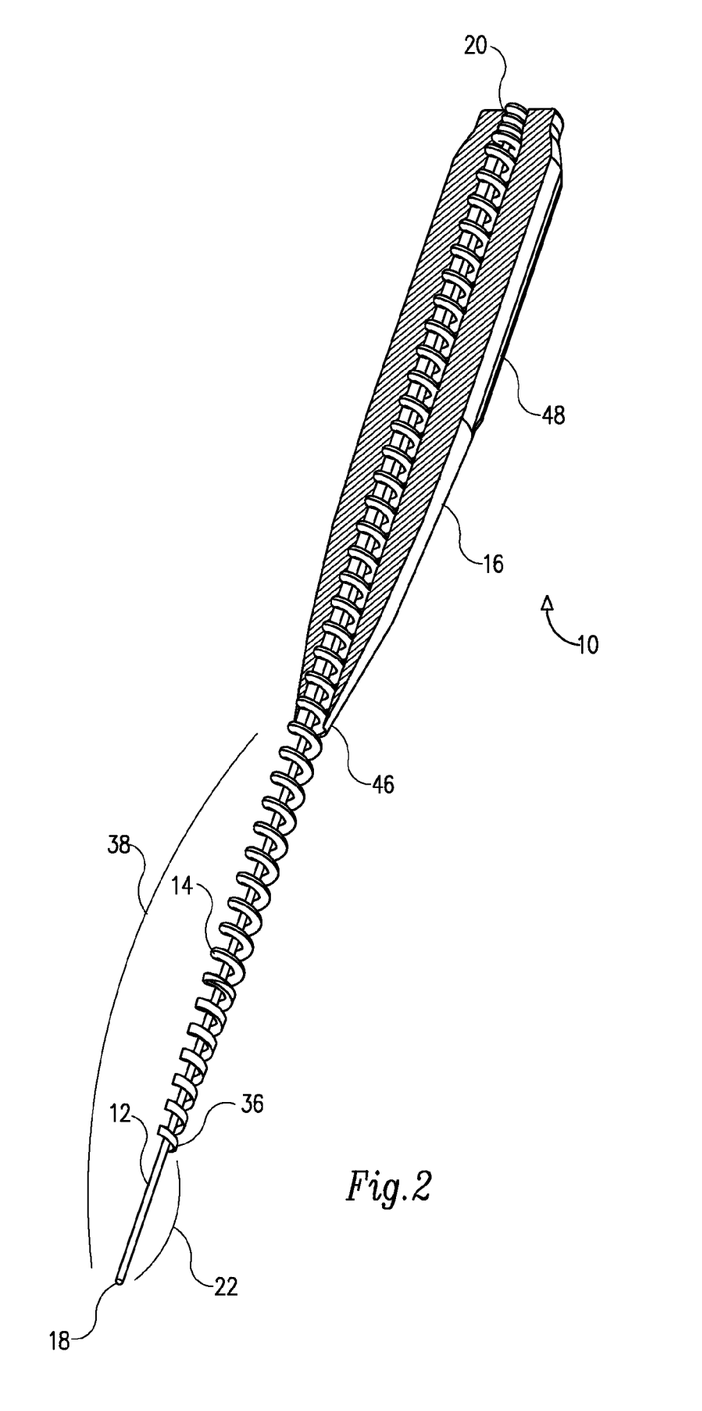
FIG. 2 is a cross-sectional perspective view of the endodontic file of FIG. 1.
Figure 8:
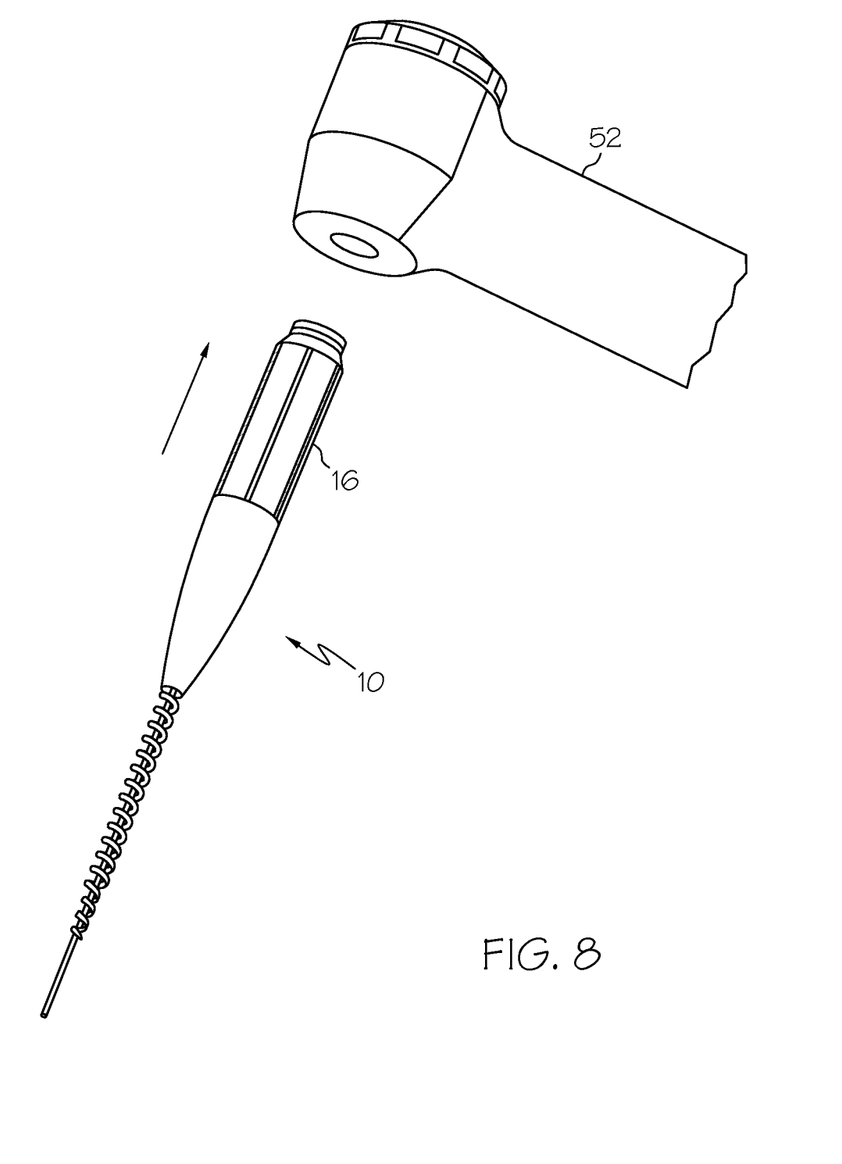
FIG. 8 is a perspective view of the file prior to insertion into a handpiece head.

FIGS. 1 and 2 show an endodontic file 10 to be utilized with a dental instrument, such as a handpiece 52 (FIG. 8) to which an elastomer grip 16 of the file 10 is attachable and supported only by friction, being slightly wider than the internal diameter of the mounting barrel of the dental instrument. The file 10 permits complete canal preparation in a single, time-saving procedure after the first canal opening is made, typically using the smallest applicable hand-held file thickness which is normally the 0.15 size. The file 10 is composed of at least three basic elements, a central longitudinal cord 12, a helically wound wire 14 at least partially surrounding the cord 12 and an elastomer grip 16 partially covering the helically wound wire 14 near a first end thereof.

Figures 3A, 3B, 3C:
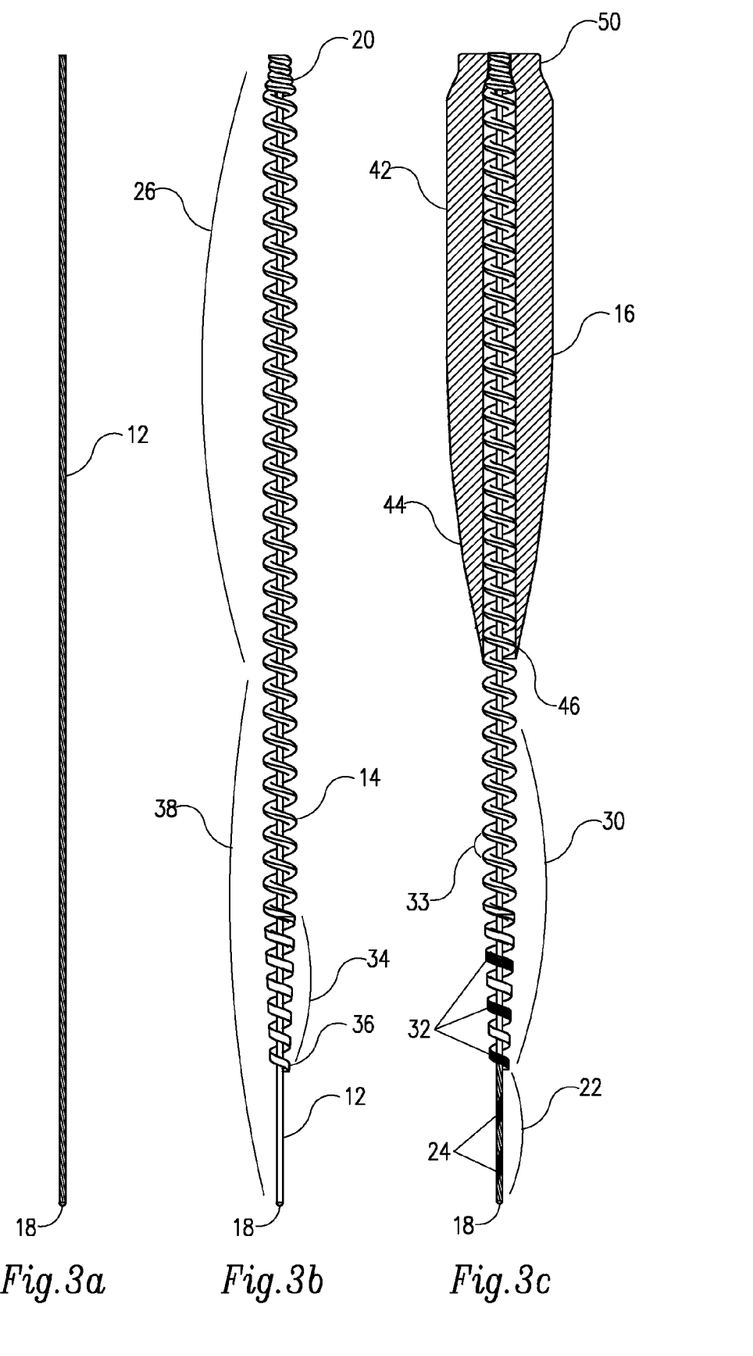
FIG. 3a shows pictorially a globule at the working end of the central longitudinal cord of the file shown in FIG. 1.
FIG. 3b shows pictorially a detail of the helically wound abrasive wire surrounding the central longitudinal cord of the file shown in FIG. 1.
FIG. 3c shows a detail of the abrasive layer of the helically wound wire shown in FIG. 3b.

With reference to FIGS. 1 to 3c, the central longitudinal cord 12 may be made of twisted thin stainless-steel wires, welded together at a first end by laser or other heating process, to form a hemispherical globule 18 preferably having the same diameter as the cord 12. A typical cord 12 is between 0.2 mm to 0.3 mm in diameter and is twisted of 15 to 25 wires. The cord 12 is firmly secured at a second end thereof to the helically wound wire 14 by tight coiling of few turns 20 of the helically wound wire 14 around the cord 12. Optionally, the cord 12 can be secured by soldering, brazing, welding or gluing to the helically wound wire 14. The cord 12 is longer than the surrounding helically wound wire 14, leaving an exposed portion 22, near the globule 18 which is coated with a circular, helical or longitudinal pattern of an abrasive layer 24 (FIG. 3c). The globule 18 has a preferably smooth finish and is not coated with abrasive layer. In one embodiment, the exposed portion 22 of the cord 12 is coated with a single circular pattern of an abrasive layer of approximately 1 mm width which is spaced apart by approximately 1 mm from the globule 18. The exposed portion 22 is of 3 mm to 6 mm in length.

The surrounding helically wound wire 14 may be made of stainless-steel having a diameter of 0.2 to 0.4 mm. The helically wound wire 14 is divided along its length into two portions, an inactive portion 26 (FIG. 3b) mostly covered by the elastomer grip 16 and an active portion 30 typically between 8 mm to 15 mm in length. At least part of the outer surface of the active portion 30 is coated with an abrasive layer 32 (FIG. 3c). In a second embodiment, at least part of the outer surface of the active portion 30 is coated with intermittent coating of an abrasive layer 32. As specifically shown in FIG. 3c, intermittent spiral coating is used so as to cover alternate coils of the helically wound wire 14. The abrasive layers 32 and 24 of the active portion 30 and the exposed portion 22 respectively, consists of abrasive particles embedded in a binder, such as thin nickel layer or elastomer binder. Common abrasives are selected from the group including aluminum oxide, silicon carbide, zirconium or diamond powder. The overall length of the active portion 30 and the exposed portion 22 constitute a working section 38 as will be further described below, typically between 12 mm to 18 mm in length. The pitch 33 (FIG. 3c) of the helically wound wire 14 particularly in the active portion 30 is larger than the wire diameter such that adjacent coils are spaced apart by a certain amount, providing additional free space for debris capture. Optionally varying pitch may be applied, such that different portions of the helically wound wire 14 accept different pitch values. At least part of the active portion 30 of the helically wound wire 14 is advantageously tapered 34 by a grinding, polishing or etching process so as to form a thinner tail 36 close in diameter to the cord 12. In another embodiment, only the tapered part 34 of the active portion 30 is at least partially coated with an abrasive layer. It will be noted however, that only the few turns 20 are tightly coiled over the cord 12, the majority by length of the helically wound wire 14 is loosely wounded over the cord 12 including the tapered portion 34 (FIG. 3b), such that an annular gap of between 0.2 mm to 0.8 mm exists between the cord 12 and the helically wound wire 14 along at least the entire length of the active portion 30. The free radial play of the cord 12 in the helically wound wire 14 contributes in preventing high strain of the cord 12 when introduced into a curved canal and to an independent operation of the cord when the helically wound wire 14 is restricted in motion as will be explained below.

The grip 16 is made of an elastomer material such as rubber or thermoplastic elastomer, preferably injection or pressure molded directly over the cord 12 and helically wound wire 14. Optionally the elastomer grip can be elastically stretched, bonded or heat shrunk over the helically wound wire 14. The grip 16 is advantageously cylindrical 42 with conical extension 44 tapering to a very thin cover 46 towards the active portion 30 of the helically wound wire 14. The conical extension 44 of the grip 16 constituting a transitional flexibility zone between the gripping cylinder 42 and the active portion 30 of the helically wound wire 14. specific hardness properties of the grip 16 material are selected to provide effective stress relieving of the helically wound wire along the conical extension 44 of the elastomer grip 16 during operation. The cylindrical portion 42 of the grip 16 is frictionally inserted into the mounting barrel of a standard or dedicated handpiece 52 (FIG. 8) for imparting rotational movement to the file, no other locking means is used. Optionally longitudinal fins 48 of the same elastomer material are formed in a circular array around the cylindrical portion 42 further improving the retention force to the handpiece barrel. It will be understood that the imparted torque is limited by the percentage of squeeze of the cylinder 42 or fins 48 during insertion to the mounting barrel and by the coefficient of friction between the grip 16 elastomer material and the metal barrel of the handpiece. Accordingly the maximal transmitted torque can be calculated or otherwise experimentally observed for any specific combination of cylinder 42 or fins 48 external diameter and elastomer raw material. Furthermore, the desired maximal transmitted torque can be precisely controlled and constantly repeated in a mass production of files 10 made in accordance with the present invention.

The grip 16 is optionally provided with a short top section 50 of reduced diameter, on which a metal cap (not shown) can be conductively attached to the central cord 12 using a conductive binder such as solder, laser weld or metal filled epoxy. The metal cap may serve as an electrical reference point for an apex locator, as known per se.

With reference to FIGS. 4a to 8, the method of usage of the file 10 is described. In operation, the file 10 is attached to a standard or dedicated handpiece 52 (FIG. 8) as described above and inserted to the root canal 54 (Fig, 5) of a tooth 56. Manual back and forth motion is provided while the handpiece is set to rotate at speed of between 6,000 to 30,000 rpm and irrigation is supplied. The slender, working section 38 of the file 10 is centrifugally thrown against the internal dentin layer 58 of the canal wall following the natural curvature and complex cross-section of the root canal in exact manner. The abrasive coating gently buffs and polishes the dentin layer 58, leaving a smooth and clean surface with no smear traces. Back and forth motion enables introduction of lubricant and rinse of debris with constant water irrigation supplied by the handpiece as known per se.

The direction of rotation of the file as shown by arrows in FIGS. 4a to 7 is in the sense that will further tighten the twist of both the cord 12 and the helically wound wire 14. It will be understood that the opposite direction that will tend to loose the twist of the cord 12 and the helically wound wire 14 is also possible providing better removal rate of debris.

Figure 4A:
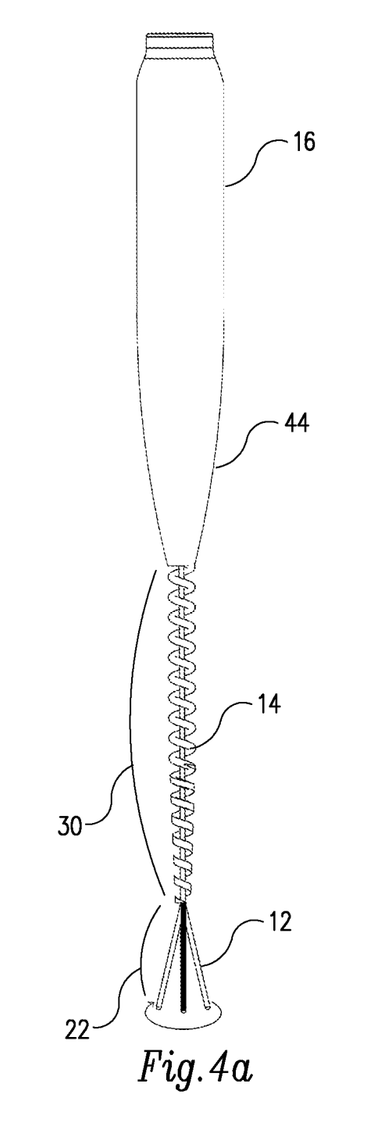
FIG. 4a shows pictorially the file in one mode of operation during rotation in a root canal.
Figure 4B:
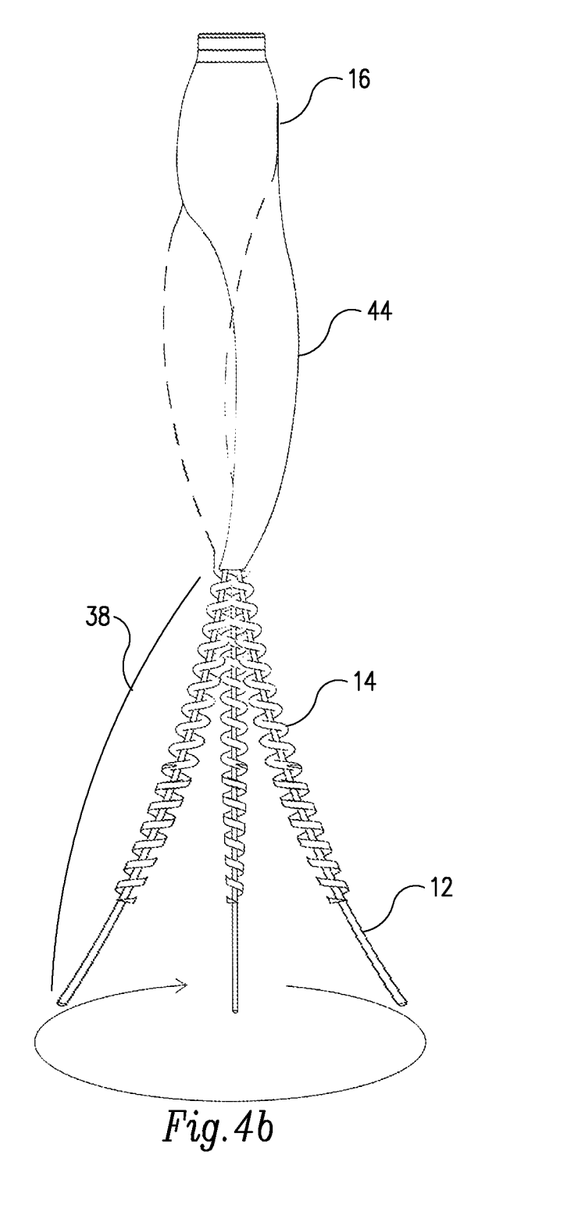
FIG. 4b shows pictorially the file in a different mode of operation during rotation in a root canal.
Figure 5:
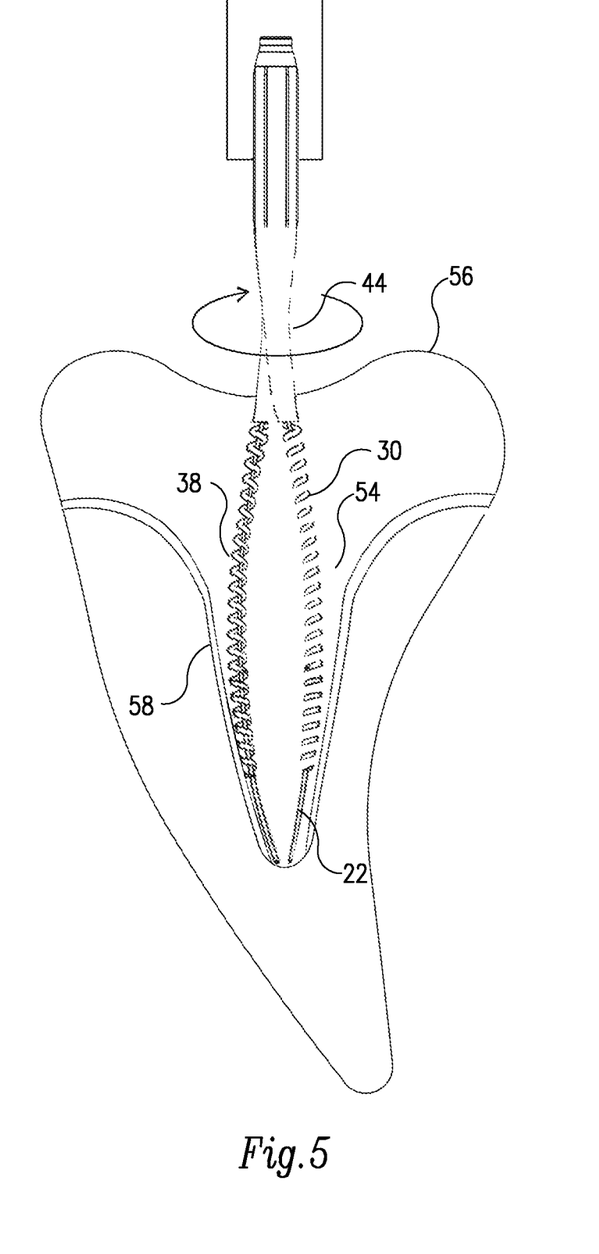
FIG. 5 is a pictorial representation showing a first mode of operation of the file in a root canal of a tooth.
Figure 6:
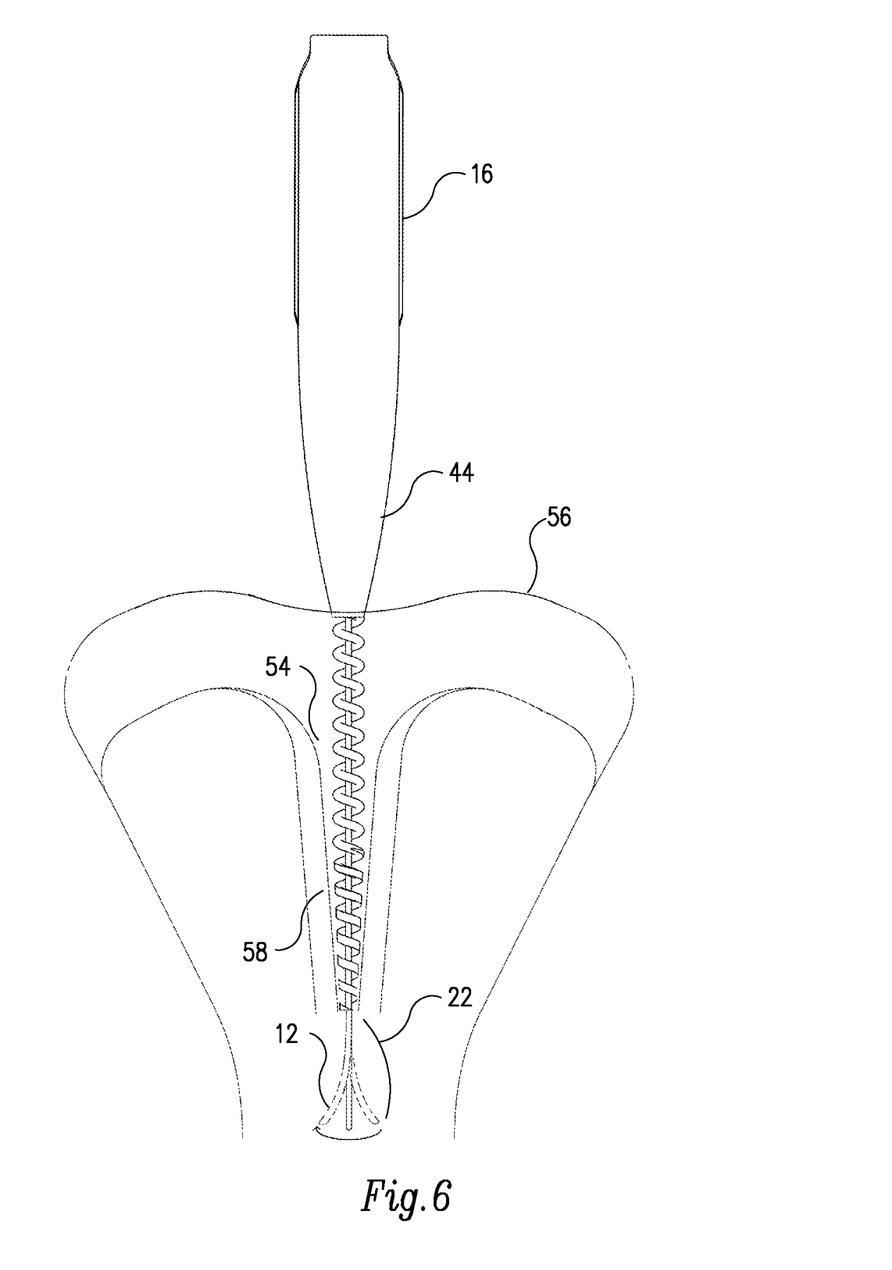
FIG. 6 is a pictorial representation showing a second mode of operation of the file in a root canal of a tooth.
Figure 7:
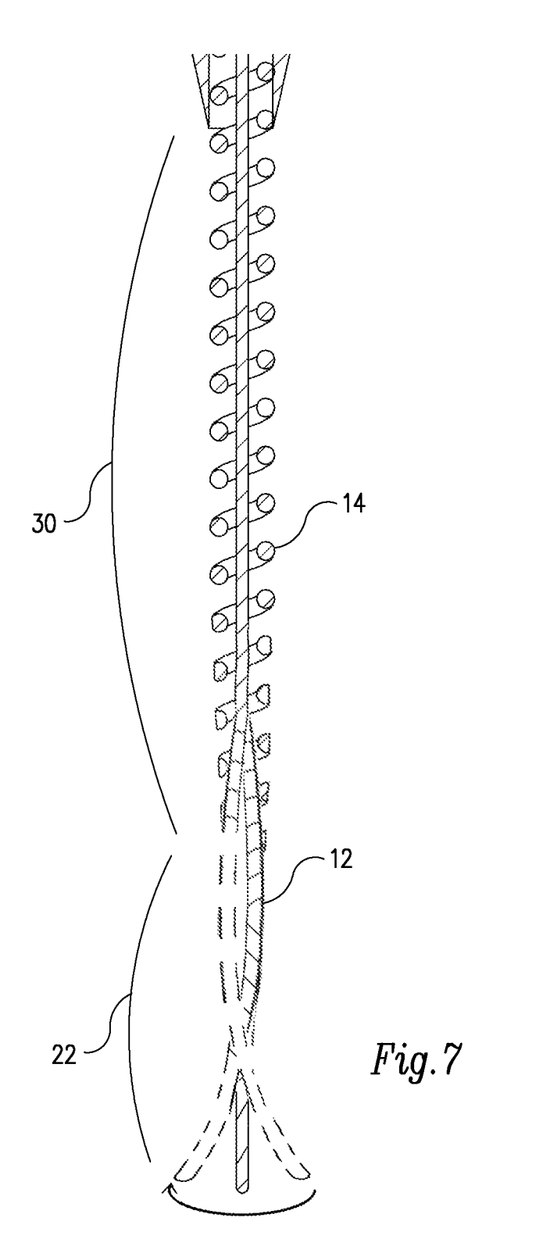
FIG. 7 is an enlarged view of an end portion of the file shown in FIG. 6.

The file 10 adopts two operation modes related to its position in the root canal, while canal penetration is in the upper portion or top two thirds, also known as Coronal third and Middle third (FIG. 5), the file will work in a first operating mode as a single flexible unit including the working portion 38 and the conical extension 44 of the grip 16 (FIG. 4b). A second operation mode is adopted as the file approaches the narrow Apical third (FIG. 6), or the lower portion of the root canal having a depth that is approximately half the depth of the upper portion wherein the motion of the helically wound wire 14 along the active portion 30 also narrows, allowing mainly the central longitudinal cord 12 to utilize its free radial play in the helically wound wire 14 and the centrifugal force to oscillate independently (FIGS. 4a, 7), facilitating penetration of the file 10 to the apical constriction widen and clean it during the same single procedure. Upon reaching the apical constriction, the globule 18 at the tip of the cord 12 is limited in space, such that even if additional circular motion is impaired it will rotate about its own axis, thus preventing perforation of the apical tissue. No significant axial force is needed during operation as related to prior art nickel-titanium files.

Transfer of torque from the handpiece to the file 10 is based only on friction. The unique effect of this method turns the file grip 16 into a sort of safety coupling. This guarantees that when the shear force between the file 10 and the root canal increases, for any reason, beyond a certain value, the grip 16 will slip in the handpiece barrel and no breakage damage will occur to the file, nor any undesirable damage to the dentin layer. The standard locking latch mechanism of the handpiece is eliminated.

It will be evident to those skilled in the art that the invention is not limited to the details of the foregoing illustrated embodiments, the scope of the invention being indicated by the appended claims.

The invention claimed is:

1. An endodontic file for use with a dental instrument having a rotatable barrel of known internal diameter, the endodontic file having a first end and a second end and being adapted for coupling at the first end thereof to the barrel of the dental instrument, the endodontic file comprising at least a central longitudinal cord, a helically wound wire at least partially surrounding the longitudinal cord, and an elastomeric grip partially covering the helically wound wire and extending from a terminal portion of the first end of the endodontic file thereof, the elastomeric grip serving to frictionally engage the rotatable barrel, whereby on insertion into the barrel, the elastomeric grip is squeezed by the barrel and the endodontic file is supported therein by friction alone without any other locking means.

2. The file as claimed in claim 1, wherein the central longitudinal cord is made of twisted thin stainless-steel wires, welded together at a first end to form a hemispherical globule.

3. The file as claimed in claim 2, wherein the globule is of equal diameter to the longitudinal cord.

4. The file as claimed in claim 1, wherein the longitudinal cord has a diameter between 0.2 mm to 0.3 mm and is twisted of 15 to 25 wires.

5. The file as claimed in claim 1, wherein the longitudinal cord is firmly secured at a second end thereof to the helically wound wire by tight coiling few turns of the helically wound wire around the longitudinal cord.

6. The file as claimed in claim 1, wherein the longitudinal cord is firmly secured at a second end thereof to the helically wound wire by any one or more of soldering, brazing, welding and gluing.

7. The file as claimed in claim 3 wherein the longitudinal cord is longer than the surrounding helically wound wire, leaving an exposed portion, near the globule which is coated with a circular, helical or longitudinal pattern of an abrasive layer.

8. The file as claimed in claim 7, wherein the exposed portion of the longitudinal cord is coated with a single circular pattern of an abrasive layer of approximately 1 mm width which is spaced apart by approximately 1 mm from the globule, the globule having a smooth finish without abrasive layer coating.

9. The file as claimed in claim 7, wherein the exposed portion is between 3 to 6 mm in length.

10. The file as claimed in claim 1, wherein the helically wound wire is made of stainless-steel having a diameter of 0.2 to 0.4 mm.

11. The file as claimed in claim 1, wherein the helically wound wire is divided along its length into an inactive portion mostly covered by the elastomeric grip and an active portion of between 8 mm to 15 mm in length, at least part of the outer surface of the active portion being coated with an abrasive layer.

12. The file as claimed in claim 11, having an intermittent spiral coating of an abrasive layer that covers alternate coils of the wire along at least part of the outer surface of the active portion.

13. The file as claimed in claim 7, wherein:
the helically wound wire is divided along its length into an inactive portion mostly covered by the elastomeric grip and an active portion of between 8 mm to 15 mm in length, at least part of the outer surface of the active portion being coated with an abrasive layer, and
the abrasive layer of the active portion and the abrasive layer of the exposed portion comprises abrasive particles embedded in a binder formed of a thin nickel layer or an elastomeric binder.

14. The file as claimed in claim 13, wherein the abrasive particles are selected from the group of aluminum oxide, silicon carbide, zirconium and diamond powder.

15. The file as claimed in claim 13, wherein a combined length of the active portion and the exposed portion constitute a working section of 12 mm to 18 mm in length.

16. The file as claimed in claim 11, wherein the helically wound wire has a pitch that is larger than the wire diameter particularly in the active portion such that adjacent coils are spaced apart by a certain amount.

17. The file as claimed in claim 16, wherein the pitch varies, such that different portions of the helically wound wire are of different pitch.

18. The file as claimed in claim 11, wherein at least part of the active portion of the helically wound wire is tapered to form a thinner tail close in diameter to that of the longitudinal cord.

19. The file as claimed in claim 18, wherein only the tapered part of the active portion is at least partially coated with an abrasive layer.

20. The file as claimed in claim 1, wherein most of the helically wound wire is loosely wounded over the longitudinal cord.

21. The file as claimed in claim 11, having an annular gap of between 0.2 mm to 0.8 mm between the longitudinal cord and the helically wound wire along at least the entire length of the active portion.

22. The file as claimed in claim 1, wherein the elastomeric material is rubber or a thermoplastic elastomer.

23. The file as claimed in claim 1, wherein the elastomeric grip is assembled over the helically wound wire using a method chosen from the list of injection molding, pressure molding, elastically stretching, bonding and heat shrinking.

24. The file as claimed in claim 11, wherein the elastomeric grip has a cylindrical end adapted for inserting into the barrel with a conical extension tapering towards the active portion of the helically wound wire.

25. The file as claimed in claim 24, having a circular array of longitudinal fins of the elastomeric material formed around the cylindrical portion of the grip.

26. The file as claimed in claim 24, wherein the elastomeric grip hardness properties are selected to provide effective stress relieving of the helically wound wire along the conical extension of the elastomer grip during operation.

27. The file as claimed in claim 1, wherein the grip is provided with a short top section of reduced diameter for accommodating a metal cap that is conductively attached to the central longitudinal cord using a conductive binder chosen from the list of solder, laser weld and metal filled epoxy.

28. The file as claimed in claim 1, wherein an outer diameter of the elastomeric grip is wider than the internal diameter of the barrel of the dental instrument with which it is intended for use.

29. An endodontic file for use with a dental instrument having a rotatable barrel of known internal diameter, the endodontic file having a first end and a second end and being adapted for coupling at the first end thereof to the barrel of the dental instrument, the endodontic file comprising at least a central longitudinal cord, a helically wound wire at least partially surrounding the longitudinal cord, and an elastomeric grip partially covering the helically wound wire at the first end of the endodontic file thereof and serving to frictionally engage the rotatable barrel, whereby on insertion into the barrel, the elastomeric grip is squeezed by the barrel and the endodontic file is supported therein by friction alone without any other locking means, wherein the elastomeric grip further comprises a top section at the first end of the endodontic file, the top section comprising an elastomeric material.

30. The endodontic file as claimed in claim 29, wherein the longitudinal cord is made of twisted thin stainless-steel wires, welded together at a first end to form a hemispherical globule.

31. The endodontic file as claimed in claim 30, wherein the longitudinal cord is longer than the surrounding helically wound wire, leaving an exposed portion, near the hemispherical globule which is coated with a circular, helical or longitudinal pattern of an abrasive layer.

32. The endodontic file as claimed in claim 31, wherein the exposed portion of the longitudinal cord is coated with a single circular pattern of an abrasive layer of approximately 1 mm width which is spaced apart by approximately 1 mm from the hemispherical globule, the hemispherical globule having a smooth finish without abrasive layer coating.

33. The endodontic file as claimed in claim 29, wherein the longitudinal cord is firmly secured at a second end thereof to the helically wound wire by tight coiling few turns of the helically wound wire around the longitudinal cord.

34. The endodontic file as claimed in claim 29, wherein the helically wound wire is divided along its length into an inactive portion mostly covered by the elastomeric grip and an active portion of between 8 mm to 15 mm in length, at least part of the outer surface of the active portion being coated with an abrasive layer.

* * * * *